United States Patent
Fong et al.

(12) 
(10) Patent No.: US 6,495,665 B1
(45) Date of Patent: Dec. 17, 2002

(54) ISOFORMS OF MOUSE SEROTONIN 5-HT2C RECEPTOR

(75) Inventors: Tong M. Fong, Somerset, NJ (US); Jie Liu, Dayton, NJ (US); Leonardus H. T. Van Der Ploeg, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/526,309

(22) Filed: Mar. 15, 2000

Related U.S. Application Data

(60) Provisional application No. 60/124,439, filed on Mar. 15, 1999.

(51) Int. Cl.$^7$ ............................................. C07K 14/705
(52) U.S. Cl. ..................... 530/350; 435/7.21; 435/69.1; 435/252.3; 435/320.1; 530/872
(58) Field of Search ................................. 530/350, 812; 435/69.1, 7.21, 252.3, 320.1

(56) References Cited

U.S. PATENT DOCUMENTS

| | | |
|---|---|---|
| 4,686,186 A | 8/1987 | Sugden |
| 5,654,139 A | 8/1997 | Lappalainen et al. |
| 5,698,766 A | 12/1997 | Julius et al. |
| 5,780,245 A | 7/1998 | Maroteaux |

FOREIGN PATENT DOCUMENTS

| | | |
|---|---|---|
| WO | WO 98/38217 | 9/1998 |

OTHER PUBLICATIONS

Julius et al. The 5HT2 receptor defines a family of structurally distrinct but functionally conserved serotonin receptors. Feb. 1990. P.N.A.S. 87:928–932.*

Julius, David, et al., "Molecular Characterization of a Functional cDNA Encoding the Serotonin 1c Receptor," *Science*, vol. 241, pp. 558–564, Jul. 29, 1998.

Saltzman, Alan G., et al., "Cloning of the Human Serotonin 5–HT2 and 5–HT1C Receptor Subtypes," *BioChemical and BioPhysical Research Communications*, vol., 181, No. 3, pp. 1469–1478, 1991.

Yu, Lei, et al., "The Mouse 5–HT1C receptor contains eight hydrophobic domains and is X–linked," *Molecular Brain Research*, 11, pp. 143–149, 1991.

Burns, Colleen M., et al., "Regulation of serotonin–2C receptor G–protein coupling by RNA editing," *Nature*, vol. 387, pp. 303–308, May 15, 1997.

\* cited by examiner

*Primary Examiner*—John Ulm
(74) *Attorney, Agent, or Firm*—Richard S. Parr; Melvin Winokur

(57) ABSTRACT

The invention includes mouse serotonin 5-HT2c receptor isoforms having amino acid replacements at one or more positions of the natural mouse serotonin 5-HT2c receptor polypeptide sequence, specifically at one or more of positions 157, 159 and 161. The polypeptides are useful for identifying ligands which bind with the serotonin 5-HT2c receptor and modulators of the serotonin 5-HT2c, and for identifying drugs with affinity for 5-HT2 receptors which are used to treat schizophrenia, Parkinsonism, and anxiety disorders.

2 Claims, No Drawings

SEQUENCE LISTING

<160> NUMBER OF SEQ ID NOS: 44

<210> SEQ ID NO 1
<211> LENGTH: 459
<212> TYPE: PRT
<213> ORGANISM: VSV Transfected 293 Cells

<400> SEQUENCE: 1

```
Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Val Arg Ser Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
        275                 280                 285
```

-continued

```
Arg Arg Lys Lys Lys Glu Lys Arg Pro Arg Gly Thr Met Gln Ala Ile
    290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
        355                 360                 365

Tyr Thr Leu Phe Asn Lys Ile Tyr Arg Arg Ala Phe Ser Lys Tyr Leu
    370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
        435                 440                 445

Ser Asn Val Val Ser Glu Arg Ile Ser Ser Val
    450                 455

<210> SEQ ID NO 2
<211> LENGTH: 1380
<212> TYPE: DNA
<213> ORGANISM: VSV Transfected 293 Cells

<400> SEQUENCE: 2
atggtgaacc tgggcactgc ggtgcgctca ctccttgtgc acctaattgg cctattggtt     60
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
tggcctttac ctagatattt gtgccccgtc tggatttcac tagatgtgct attttcaact    420
gcgtccatca tgcacctctg cgccatatcg ctggaccggt atgtagcagt gcgtagtcct    480
gttgagcata gccggttcaa ttcgcggact aaggccatca tgaagattgc catcgtttgg    540
gcaatatcaa taggagtttc agttcctatc cctgtgattg gactgaggga cgaaagcaaa    600
gtgttcgtga ataatactac ctgcgtgctc aatgacccga acttcgttct catcgggtcc    660
ttcgtggcat tcttcatccc gttgacaatt atggtgatca cctacttctt aacgatctac    720
gtcctacgcc gtcaaaccct gatgttactt cgaggtcaca ccgaggagga actgcgtaat    780
atcagcctga actttctaaa gtgctgctgc aagaagggtg atgaggaaga gaacgctccc    840
aaccccaatc cagatcagaa gccacgtcga aagaagaaag aaaagcggcc tagaggcacc    900
atgcaagcta tcaacaatga gaagaaagct tccaaagtcc ttggcattgt attctttgtg    960
tttctgatca tgtggtgccc gtttttcatc accaatatcc tgtcggtgct ttgtgggaag   1020
gcctgtaacc aaaagctaat ggagaaactt ctcaatgtgt ttgtttggat tggctatgtg   1080
tgttcaggca tcaatcctct ggtgtacact ctcttcaaca aaatttaccg aagggctttc   1140
```

-continued

```
tctaaatatt tgcgctgcga ttataagcca gacaaaaagc ctcctgttcg acagattcct    1200
agggttgctg ccactgcttt gtctgggagg gagctcaatg ttaacattta tcggcatacc    1260
aatgaacgtg tagttaggaa agctaatgac acagagcctg catagagat  gcaggtagag    1320 aatttagagc tgccggtcaa tccctctaat gtggtcagcg agaggattag tagtgtgtaa    1380
```

<210> SEQ ID NO 3
<211> LENGTH: 459
<212> TYPE: PRT
<213> ORGANISM: VNV Transfected 293 Cells

<400> SEQUENCE: 3

```
Met Val Asn Leu Gly Thr Ala Val Arg Ser Leu Leu Val His Leu Ile
  1               5                  10                  15

Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
         35                  40                  45

Phe Pro Asp Gly Val Gln Asn Trp Pro Ala Leu Ser Ile Val Val Ile
 50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
130                 135                 140

His Leu Cys Ala Ile Ser Leu Asp Arg Tyr Val Ala Val Arg Asn Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Asn Ala Pro Asn Pro Asn Pro Asp Gln Lys Pro
        275                 280                 285

Arg Arg Lys Lys Lys Glu Lys Arg Pro Arg Gly Thr Met Gln Ala Ile
    290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335
```

```
Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
            370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
            450                 455

<210> SEQ ID NO 4
<211> LENGTH: 1380
<212> TYPE: DNA
<213> ORGANISM: VNV Transfected 293 Cells

<400> SEQUENCE: 4
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg acggggtac aaaactggcc agcactttca      180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcagt gcgtaatcct     480
gttgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga aacgctcccc     840
aaccccaatc cagatcagaa gccacgtcga agaagaaag aaaagcggcc tagaggcacc     900
atgcaagcta tcaacaatga agaaagct tccaaagtcc ttggcattgt attctttgtg     960
tttctgatca tgtggtgccc gttttcatc accaatatcc tgtcggtgct tgtgggaag    1020
gcctgtaacc aaaagctaat ggagaaactt ctcaatgtgt tgtttggat ggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
agggttgctg ccactgctt gtctgggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

-continued

```
<210> SEQ ID NO 5
<211> LENGTH: 459
<212> TYPE: PRT
<213> ORGANISM: VDV Transfected 293 Cells

<400> SEQUENCE: 5

Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Val Arg Asp Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
        275                 280                 285

Arg Arg Lys Lys Lys Glu Lys Arg Pro Arg Gly Thr Met Gln Ala Ile
    290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
        355                 360                 365

Tyr Thr Leu Phe Asn Lys Ile Tyr Arg Arg Ala Phe Ser Lys Tyr Leu
    370                 375                 380
```

-continued

```
Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
        435                 440                 445

Ser Asn Val Val Ser Glu Arg Ile Ser Ser Val
    450                 455

<210> SEQ ID NO 6
<211> LENGTH: 1380
<212> TYPE: DNA
<213> ORGANISM: VDV Transfected 293 Cells

<400> SEQUENCE: 6
atggtgaacc tgggcactgc ggtgcgctca ctccttgtgc acctaattgg cctattggtt     60
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
tggcctttac ctagatattt gtgccccgtc tggatttcac tagatgtgct attttcaact    420
gcgtccatca tgcacctctg cgccatatcg ctggaccggt atgtagcagt gcgtgatcct    480
gttgagcata gccggttcaa ttcgcggact aaggccatca tgaagattgc catcgtttgg    540
gcaatatcaa taggagtttc agttcctatc cctgtgattg gactgaggga cgaaagcaaa    600
gtgttcgtga ataatactac ctgcgtgctc aatgacccga acttcgttct catcgggtcc    660
ttcgtggcat tcttcatccc gttgacaatt atggtgatca cctacttctt aacgatctac    720
gtcctacgcc gtcaaaccct gatgttactt cgaggtcaca ccgaggagga actgcgtaat    780
atcagcctga actttctaaa gtgctgctgc aagaagggtg atgaggaaga gaacgctccc    840
aaccccaatc cagatcagaa gccacgtcga aagaagaaag aaaagcggcc tagaggcacc    900
atgcaagcta tcaacaatga gaagaaagct tccaaagtcc ttggcattgt attctttgtg    960
tttctgatca tgtggtgccc gtttttcatc accaatatcc tgtcggtgct ttgtgggaag   1020
gcctgtaacc aaaagctaat ggagaaactt ctcaatgtgt ttgtttggat tggctatgtg   1080
tgttcaggca tcaatcctct ggtgtacact ctcttcaaca aaatttaccg aagggctttc   1140
tctaaatatt tgcgctgcga ttataagcca gacaaaaagc ctcctgttcg acagattcct   1200
agggttgctg ccactgcttt gtctgggagg gagctcaatg ttaacattta tcggcatacc   1260
aatgaacgtg tagttaggaa agctaatgac acagagcctg gcatagagat gcaggtagag   1320
aatttagagc tgccggtcaa tccctctaat gtggtcagcg agaggattag tagtgtgtaa   1380

<210> SEQ ID NO 7
<211> LENGTH: 459
<212> TYPE: PRT
<213> ORGANISM: VSI Transfected 293 Cells

<400> SEQUENCE: 7

Met Val Asn Leu Gly Thr Ala Val Arg Ser Leu Leu Val His Leu Ile
 1               5                  10                  15
```

-continued

```
Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
             35                  40                  45

Phe Pro Asp Gly Val Gln Asn Trp Pro Ala Leu Ser Ile Val Val Ile
 50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
                100                 105                 110

Leu Ala Ile Leu Tyr Asp Tyr Val Trp Pro Leu Pro Arg Tyr Leu Cys
                115                 120                 125

Pro Val Trp Ile Ser Leu Asp Val Leu Phe Ser Thr Ala Ser Ile Met
130                 135                 140

His Leu Cys Ala Ile Ser Leu Asp Arg Tyr Val Ala Val Arg Ser Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
                180                 185                 190

Ile Gly Leu Arg Asp Glu Ser Lys Val Phe Val Asn Asn Thr Thr Cys
                195                 200                 205

Val Leu Asn Asp Pro Asn Phe Val Leu Ile Gly Ser Phe Val Ala Phe
                210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Arg Gly His Thr Glu Glu
                245                 250                 255

Glu Leu Arg Asn Ile Ser Leu Asn Phe Leu Lys Cys Cys Cys Lys Lys
                260                 265                 270

Gly Asp Glu Glu Glu Asn Ala Pro Asn Pro Asn Pro Asp Gln Lys Pro
                275                 280                 285

Arg Arg Lys Lys Lys Glu Lys Arg Pro Arg Gly Thr Met Gln Ala Ile
                290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
                340                 345                 350

Val Phe Val Trp Ile Gly Tyr Val Cys Ser Gly Ile Asn Pro Leu Val
                355                 360                 365

Tyr Thr Leu Phe Asn Lys Ile Tyr Arg Arg Ala Phe Ser Lys Tyr Leu
                370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
                420                 425                 430
```

```
Pro Gly Ile Glu Met Gln Val Glu Asn Leu Glu Leu Pro Val Asn Pro
        435                 440                 445

Ser Asn Val Val Ser Glu Arg Ile Ser Ser Val
    450                 455

<210> SEQ ID NO 8
<211> LENGTH: 1380
<212> TYPE: DNA
<213> ORGANISM: VSI Transfected 293 Cells

<400> SEQUENCE: 8
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg gcaacattc tcgttatcat ggcagtaagc      240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcagt gcgtagtcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga cttcgttct catcgggtcc      660 ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga gaacgctccc     840
aaccccaatc cagatcagaa gccacgtcga agaagaaag aaaagcggcc tagaggcacc      900
atgcaagcta tcaacaatga gaagaaagct tccaaagtcc ttggcattgt attctttgtg     960
tttctgatca tgtggtgccc gttttttcatc accaatatcc tgtcggtgct ttgtgggaag    1020
gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
agggttgctg ccactgcttt gtctggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380

<210> SEQ ID NO 9
<211> LENGTH: 459
<212> TYPE: PRT
<213> ORGANISM: MNI Transfected 293 Cells

<400> SEQUENCE: 9

Met Val Asn Leu Gly Thr Ala Val Arg Ser Leu Val His Leu Ile
  1               5                  10                  15

Gly Leu Leu Val Trp Gln Phe Asp Ile Ser Ile Ser Pro Val Ala Ala
                 20                  25                  30

Ile Val Thr Asp Thr Phe Asn Ser Ser Asp Gly Gly Arg Leu Phe Gln
             35                  40                  45

Phe Pro Asp Gly Val Gln Asn Trp Pro Ala Leu Ser Ile Val Val Ile
     50                  55                  60
```

-continued

```
Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
            115                 120                 125

Pro Val Trp Ile Ser Leu Asp Val Leu Phe Ser Thr Ala Ser Ile Met
130                 135                 140

His Leu Cys Ala Ile Ser Leu Asp Arg Tyr Val Ala Met Arg Asn Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Asn Ala Pro Asn Pro Asn Pro Asp Gln Lys Pro
            275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
450                 455
```

-continued

<210> SEQ ID NO 10
<211> LENGTH: 1380
<212> TYPE: DNA
<213> ORGANISM: MNI Transfected 293 Cells

<400> SEQUENCE: 10

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg acgcttgtt tcaattcccg acgggtac aaaactggcc agcactttca       180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggccttta ctagatattt gtgccccgtc tggatttcac tagatgtgct attttcaact       420
gcgtccatca tgcacctctg cgccatatcg ctggaccggt atgtagcaat gcgtaatcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
tcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga aacgctccc      840
aaccccaatc cagatcagaa gccacgtcga agaagaaag aaaagcggcc tagaggcacc       900
atgcaagcta tcaacaatga aagaaagct tccaaagtcc ttggcattgt attctttgtg      960
tttctgatca tgtggtgccc gtttttcatc accaatatcc tgtcggtgct tgtgggaag    1020
gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
aggggttgctg ccactgcttt gtctgggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

<210> SEQ ID NO 11
<211> LENGTH: 459
<212> TYPE: PRT
<213> ORGANISM: INV Transfected 293 Cells

<400> SEQUENCE: 11

```
Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95
```

```
Ala Ile Ala Asp Met Leu Val Gly Leu Leu Val Met Pro Leu Ser Leu
            100                 105                 110
Leu Ala Ile Leu Tyr Asp Tyr Val Trp Pro Leu Pro Arg Tyr Leu Cys
        115                 120                 125
Pro Val Trp Ile Ser Leu Asp Val Leu Phe Ser Thr Ala Ser Ile Met
130                 135                 140
His Leu Cys Ala Ile Ser Leu Asp Arg Tyr Val Ala Ile Arg Asn Pro
145                 150                 155                 160
Val Glu His Ser Arg Phe Asn Ser Arg Thr Lys Ala Ile Met Lys Ile
                165                 170                 175
Ala Ile Val Trp Ala Ile Ser Ile Gly Val Ser Val Pro Ile Pro Val
            180                 185                 190
Ile Gly Leu Arg Asp Glu Ser Lys Val Phe Val Asn Asn Thr Thr Cys
        195                 200                 205
Val Leu Asn Asp Pro Asn Phe Val Leu Ile Gly Ser Phe Val Ala Phe
210                 215                 220
Phe Ile Pro Leu Thr Ile Met Val Ile Thr Tyr Phe Leu Thr Ile Tyr
225                 230                 235                 240
Val Leu Arg Arg Gln Thr Leu Met Leu Leu Arg Gly His Thr Glu Glu
                245                 250                 255
Glu Leu Arg Asn Ile Ser Leu Asn Phe Leu Lys Cys Cys Cys Lys Lys
            260                 265                 270
Gly Asp Glu Glu Glu Asn Ala Pro Asn Pro Asn Pro Asp Gln Lys Pro
        275                 280                 285
Arg Arg Lys Lys Lys Glu Lys Arg Pro Arg Gly Thr Met Gln Ala Ile
290                 295                 300
Asn Asn Glu Lys Lys Ala Ser Lys Val Leu Gly Ile Val Phe Phe Val
305                 310                 315                 320
Phe Leu Ile Met Trp Cys Pro Phe Phe Ile Thr Asn Ile Leu Ser Val
                325                 330                 335
Leu Cys Gly Lys Ala Cys Asn Gln Lys Leu Met Glu Lys Leu Leu Asn
            340                 345                 350
Val Phe Val Trp Ile Gly Tyr Val Cys Ser Gly Ile Asn Pro Leu Val
        355                 360                 365
Tyr Thr Leu Phe Asn Lys Ile Tyr Arg Arg Ala Phe Ser Lys Tyr Leu
370                 375                 380
Arg Cys Asp Tyr Lys Pro Asp Lys Lys Pro Pro Val Arg Gln Ile Pro
385                 390                 395                 400
Arg Val Ala Ala Thr Ala Leu Ser Gly Arg Glu Leu Asn Val Asn Ile
                405                 410                 415
Tyr Arg His Thr Asn Glu Arg Val Val Arg Lys Ala Asn Asp Thr Glu
            420                 425                 430
Pro Gly Ile Glu Met Gln Val Glu Asn Leu Glu Leu Pro Val Asn Pro
        435                 440                 445
Ser Asn Val Val Ser Glu Arg Ile Ser Ser Val
    450                 455

<210> SEQ ID NO 12
<211> LENGTH: 1380
<212> TYPE: DNA
<213> ORGANISM: INV Transfected 293 Cells

<400> SEQUENCE: 12
atggtgaacc tgggcactgc ggtgcgctca ctccttgtgc acctaattgg cctattggtt      60
```

-continued

```
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
tggcctttac ctagatattt gtgccccgtc tggatttcac tagatgtgct attttcaact    420
gcgtccatca tgcacctctg cgccatatcg ctggaccggt atgtagcaat acgtaatcct    480
gttgagcata gccggttcaa ttcgcggact aaggccatca tgaagattgc catcgtttgg    540
gcaatatcaa taggagtttc agttcctatc cctgtgattg gactgaggga cgaaagcaaa    600
gtgttcgtga ataatactac ctgcgtgctc aatgacccga acttcgttct catcgggtcc    660
ttcgtggcat tcttcatccc gttgacaatt atggtgatca cctacttctt aacgatctac    720
gtcctacgcc gtcaaaccct gatgttactt cgaggtcaca ccgaggagga actgcgtaat    780
atcagcctga actttctaaa gtgctgctgc aagaagggtg atgaggaaga gaacgctccc    840
aaccccaatc cagatcagaa gccacgtcga aagaagaaag aaaagcggcc tagaggcacc    900
atgcaagcta tcaacaatga gaagaaagct tccaaagtcc ttggcattgt attctttgtg    960
tttctgatca tgtggtgccc gtttttcatc accaatatcc tgtcggtgct ttgtgggaag   1020
gcctgtaacc aaaagctaat ggagaaactt ctcaatgtgt ttgtttggat tggctatgtg   1080
tgttcaggca tcaatcctct ggtgtacact ctcttcaaca aaatttaccg aagggctttc   1140
tctaaatatt tgcgctgcga ttataagcca gacaaaaagc ctcctgttcg acagattcct   1200
agggttgctg ccactgcttt gtctgggagg gagctcaatg ttaacattta tcggcatacc   1260
aatgaacgtg tagttaggaa agctaatgac acagagcctg gcatagagat gcaggtagag   1320
aatttagagc tgccggtcaa tccctctaat gtggtcagcg agaggattag tagtgtgtaa   1380
```

```

<210> SEQ ID NO 13
<211> LENGTH: 459
<212> TYPE: PRT
<213> ORGANISM: MDV Transfected 293 Cells
<400> SEQUENCE: 13

Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140
```

-continued

```
His Leu Cys Ala Ile Ser Leu Asp Arg Tyr Val Ala Met Arg Asp Pro
145                 150                 155                 160

Val Glu His Ser Arg Phe Asn Ser Arg Thr Lys Ala Ile Met Lys Ile
            165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
            245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
            275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
            325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
            405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
    450                 455
```

<210> SEQ ID NO 14
<211> LENGTH: 1380
<212> TYPE: DNA
<213> ORGANISM: MDV Transfected 293 Cells

<400> SEQUENCE: 14

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
```

-continued

```
tggcctttac ctagatattt gtgccccgtc tggatttcac tagatgtgct attttcaact      420
gcgtccatca tgcacctctg cgccatatcg ctggaccggt atgtagcaat gcgtgatcct      480
gttgagcata gccggttcaa ttcgcggact aaggccatca tgaagattgc catcgtttgg      540
gcaatatcaa taggagtttc agttcctatc cctgtgattg gactgaggga cgaaagcaaa      600
gtgttcgtga ataatactac ctgcgtgctc aatgacccga acttcgttct catcgggtcc      660
ttcgtggcat tcttcatccc gttgacaatt atggtgatca cctacttctt aacgatctac      720
gtcctacgcc gtcaaaccct gatgttactt cgaggtcaca ccgaggagga actgcgtaat      780
atcagcctga actttctaaa gtgctgctgc aagaagggtg atgaggaaga aacgctccc      840
aaccccaatc cagatcagaa gccacgtcga agaagaaag aaaagcggcc tagaggcacc      900
atgcaagcta tcaacaatga agaaagct tccaaagtcc ttggcattgt attctttgtg      960
tttctgatca tgtggtgccc gttttcatc accaatatcc tgtcggtgct ttgtgggaag     1020
gcctgtaacc aaaagctaat ggagaaactt ctcaatgtgt ttgtttggat tggctatgtg     1080
tgttcaggca tcaatcctct ggtgtacact ctcttcaaca aaatttaccg aagggctttc     1140
tctaaatatt tgcgctgcga ttataagcca gacaaaaagc ctcctgttcg acagattcct     1200
agggttgctg ccactgcttt gtctgggagg gagctcaatg ttaacattta tcggcatacc     1260
aatgaacgtg tagttaggaa agctaatgac acagagcctg gcatagagat gcaggtagag     1320
aatttagagc tgccggtcaa tccctctaat gtggtcagcg agaggattag tagtgtgtaa     1380
```

```
<210> SEQ ID NO 15
<211> LENGTH: 461
<212> TYPE: PRT
<213> ORGANISM: MDI Transfected 293 Cells

<400> SEQUENCE: 15

Met Val Asn Leu Gly Thr Ala Val Arg Ser Leu Val His Leu Ile
 1               5                  10                  15

Gly Leu Leu Val Trp Gln Phe Asp Ile Ser Ile Ser Pro Val Ala Ala
                20                  25                  30

Ile Val Thr Asp Thr Phe Asn Ser Ser Asp Gly Gly Arg Leu Phe Gln
            35                  40                  45

Phe Pro Asp Gly Val Gln Asn Trp Pro Ala Leu Ser Ile Val Val Ile
        50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Met Arg Asp Pro
145                 150                 155                 160

Ile Leu Glu Glu His Ser Arg Phe Asn Ser Arg Thr Lys Ala Ile Met
                165                 170                 175

Lys Ile Ala Ile Val Trp Ala Ile Ser Ile Gly Val Ser Val Pro Ile
            180                 185                 190
```

```
Pro Val Ile Gly Leu Arg Asp Glu Ser Lys Val Phe Val Asn Asn Thr
        195                 200                 205
Thr Cys Val Leu Asn Asp Pro Asn Phe Val Leu Ile Gly Ser Phe Val
210                 215                 220
Ala Phe Phe Ile Pro Leu Thr Ile Met Val Ile Thr Tyr Phe Leu Thr
225                 230                 235                 240
Ile Tyr Val Leu Arg Arg Gln Thr Leu Met Leu Leu Arg Gly His Thr
            245                 250                 255
Glu Glu Glu Leu Arg Asn Ile Ser Leu Asn Phe Leu Lys Cys Cys Cys
            260                 265                 270
Lys Lys Gly Asp Glu Glu Asn Ala Pro Asn Pro Asn Pro Asp Gln
        275                 280                 285
Lys Pro Arg Arg Lys Lys Glu Lys Arg Pro Arg Gly Thr Met Gln
        290                 295                 300
Ala Ile Asn Asn Glu Lys Lys Ala Ser Lys Val Leu Gly Ile Val Phe
305                 310                 315                 320
Phe Val Phe Leu Ile Met Trp Cys Pro Phe Phe Ile Thr Asn Ile Leu
                325                 330                 335
Ser Val Leu Cys Gly Lys Ala Cys Asn Gln Lys Leu Met Glu Lys Leu
                340                 345                 350
Leu Asn Val Phe Val Trp Ile Gly Tyr Val Cys Ser Gly Ile Asn Pro
            355                 360                 365
Leu Val Tyr Thr Leu Phe Asn Lys Ile Tyr Arg Arg Ala Phe Ser Lys
370                 375                 380
Tyr Leu Arg Cys Asp Tyr Lys Pro Asp Lys Lys Pro Pro Val Arg Gln
385                 390                 395                 400
Ile Pro Arg Val Ala Ala Thr Ala Leu Ser Gly Arg Glu Leu Asn Val
                405                 410                 415
Asn Ile Tyr Arg His Thr Asn Glu Arg Val Val Arg Lys Ala Asn Asp
            420                 425                 430
Thr Glu Pro Gly Ile Glu Met Gln Val Glu Asn Leu Glu Leu Pro Val
        435                 440                 445
Asn Pro Ser Asn Val Val Ser Glu Arg Ile Ser Ser Val
450                 455                 460

<210> SEQ ID NO 16
<211> LENGTH: 1380
<212> TYPE: DNA
<213> ORGANISM: MDI Transfected 293 Cells

<400> SEQUENCE: 16
atggtgaacc tgggcactgc ggtgcgctca ctccttgtgc acctaattgg cctattggtt      60
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
tggcctttac ctagatattt gtgccccgtc tggatttcac tagatgtgct attttcaact    420
gcgtccatca tgcacctctg cgccatatcg ctggaccggt atgtagcaat gcgtgatcct    480
attgagcata gccggttcaa ttcgcggact aaggccatca tgaagattgc catcgtttgg    540
gcaatatcaa taggagtttc agttcctatc cctgtgattg gactgaggga cgaaagcaaa    600
```

-continued

```
gtgttcgtga ataatactac ctgcgtgctc aatgacccga acttcgttct catcgggtcc   660
ttcgtggcat tcttcatccc gttgacaatt atggtgatca cctacttctt aacgatctac   720
gtcctacgcc gtcaaaccct gatgttactt cgaggtcaca ccgaggagga actgcgtaat   780
atcagcctga actttctaaa gtgctgctgc aagaagggtg atgaggaaga aacgctccc   840 aaccccaatc cagatcagaa gccacgtcga agaagaaag aaaagcggcc tagaggcacc   900
atgcaagcta tcaacaatga aagaaagct tccaaagtcc ttggcattgt attctttgtg   960
tttctgatca tgtggtgccc gttttcatc accaatatcc tgtcggtgct ttgtgggaag   1020
gcctgtaacc aaaagctaat ggagaaactt ctcaatgtgt ttgtttggat tggctatgtg   1080
tgttcaggca tcaatcctct ggtgtacact ctcttcaaca aaatttaccg aagggctttc   1140
tctaaatatt tgcgctgcga ttataagcca gacaaaaagc ctcctgttcg acagattcct   1200
agggttgctg ccactgcttt gtctgggagg gagctcaatg ttaacattta tcggcatacc   1260
aatgaacgtg tagttaggaa agctaatgac acagagcctg gcatagagat gcaggtagag   1320
aatttagagc tgccggtcaa tccctctaat gtggtcagcg agaggattag tagtgtgtaa   1380
```

<210> SEQ ID NO 17
<211> LENGTH: 459
<212> TYPE: PRT
<213> ORGANISM: MGV Transfected 293 Cells

<400> SEQUENCE: 17

```
Met Val Asn Leu Gly Thr Ala Val Arg Ser Leu Val His Leu Ile
  1               5                  10                  15

Gly Leu Leu Val Trp Gln Phe Asp Ile Ser Ile Ser Pro Val Ala Ala
                 20                  25                  30

Ile Val Thr Asp Thr Phe Asn Ser Ser Asp Gly Gly Arg Leu Phe Gln
             35                  40                  45

Phe Pro Asp Gly Val Gln Asn Trp Pro Ala Leu Ser Ile Val Val Ile
     50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Met Arg Gly Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240
```

```
Val Leu Arg Arg Gln Thr Leu Met Leu Arg Gly His Thr Glu Glu
             245                 250                 255

Glu Leu Arg Asn Ile Ser Leu Asn Phe Leu Lys Cys Cys Lys Lys
             260                 265                 270

Gly Asp Glu Glu Asn Ala Pro Asn Pro Asn Pro Asp Gln Lys Pro
             275                 280                 285

Arg Arg Lys Lys Lys Glu Lys Arg Pro Arg Gly Thr Met Gln Ala Ile
             290                 295                 300

Asn Asn Glu Lys Lys Ala Ser Lys Val Leu Gly Ile Val Phe Phe Val
305                  310                 315                 320

Phe Leu Ile Met Trp Cys Pro Phe Phe Ile Thr Asn Ile Leu Ser Val
                 325                 330                 335

Leu Cys Gly Lys Ala Cys Asn Gln Lys Leu Met Glu Lys Leu Leu Asn
                 340                 345                 350

Val Phe Val Trp Ile Gly Tyr Val Cys Ser Gly Ile Asn Pro Leu Val
                 355                 360                 365

Tyr Thr Leu Phe Asn Lys Ile Tyr Arg Arg Ala Phe Ser Lys Tyr Leu
             370                 375                 380

Arg Cys Asp Tyr Lys Pro Asp Lys Lys Pro Pro Val Arg Gln Ile Pro
385                  390                 395                 400

Arg Val Ala Ala Thr Ala Leu Ser Gly Arg Glu Leu Asn Val Asn Ile
                 405                 410                 415

Tyr Arg His Thr Asn Glu Arg Val Val Arg Lys Ala Asn Asp Thr Glu
             420                 425                 430

Pro Gly Ile Glu Met Gln Val Glu Asn Leu Glu Leu Pro Val Asn Pro
             435                 440                 445

Ser Asn Val Val Ser Glu Arg Ile Ser Ser Val
    450                 455

<210> SEQ ID NO 18
<211> LENGTH: 1380
<212> TYPE: DNA
<213> ORGANISM: MGV Transfected 293 Cells

<400> SEQUENCE: 18
atggtgaacc tgggcactgc ggtgcgctca ctccttgtgc acctaattgg cctattggtt     60
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
tggcctttac ctagatattt tgtccccgtc tggatttcac tagatgtgct attttcaact    420
gcgtccatca tgcacctctg cgccatatcg ctggaccggt atgtagcaat gcgtggtcct    480
gttgagcata gccggttcaa ttcgcggact aaggccatca tgaagattgc catcgtttgg    540
gcaatatcaa taggagtttc agttcctatc cctgtgattg gactgaggga cgaaagcaaa    600
gtgttcgtga ataatactac ctgcgtgctc aatgacccga acttcgttct catcgggtcc    660
ttcgtggcat tcttcatccc gttgacaatt atggtgatca cctacttctt aacgatctac    720
gtcctacgcc gtcaaaccct gatgttactt cgaggtcaca ccgaggagga actgcgtaat    780
atcagcctga actttctaaa gtgctgctgc aagaagggtg atgaggaaga aacgctcccc    840
aaccccaatc cagatcagaa gccacgtcga agaagaaag aaaagcggcc tagaggcacc    900
```

-continued

```
atgcaagcta tcaacaatga aagaaaagct tccaaagtcc ttggcattgt attctttgtg    960
tttctgatca tgtggtgccc gttttcatc accaatatcc tgtcggtgct tgtgggaag    1020 gcctgtaacc aaaagctaat ggagaaactt ctcaatgtgt ttgtttggat ggctatgtg    1080 tgttcaggca tcaatcctct ggtgtacact ctcttcaaca aaatttaccg aagggctttc    1140
tctaaatatt tgcgctgcga ttataagcca gacaaaaagc tcctgttcg acagattcct    1200 agggttgctg ccactgcttt gtctgggagg gagctcaatg ttaacattta tcggcatacc    1260
aatgaacgtg tagttaggaa agctaatgac acagagcctg catagagat gcaggtagag    1320 aatttagagc tgccggtcaa tccctctaat gtggtcagcg agaggattag tagtgtgtaa    1380
```

<210> SEQ ID NO 19
<211> LENGTH: 459
<212> TYPE: PRT
<213> ORGANISM: MGI Transfected 293 Cells

<400> SEQUENCE: 19

```
Met Val Asn Leu Gly Thr Ala Val Arg Ser Leu Leu Val His Leu Ile
  1               5                  10                  15

Gly Leu Leu Val Trp Gln Phe Asp Ile Ser Ile Ser Pro Val Ala Ala
             20                  25                  30

Ile Val Thr Asp Thr Phe Asn Ser Ser Asp Gly Arg Leu Phe Gln
         35                  40                  45

Phe Pro Asp Gly Val Gln Asn Trp Pro Ala Leu Ser Ile Val Val Ile
     50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Met Arg Gly Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
        275                 280                 285
```

```
Arg Arg Lys Lys Lys Glu Lys Arg Pro Arg Gly Thr Met Gln Ala Ile
        290                 295                 300
Asn Asn Glu Lys Lys Ala Ser Lys Val Leu Gly Ile Val Phe Phe Val
305                 310                 315                 320
Phe Leu Ile Met Trp Cys Pro Phe Phe Ile Thr Asn Ile Leu Ser Val
                325                 330                 335
Leu Cys Gly Lys Ala Cys Asn Gln Lys Leu Met Glu Lys Leu Leu Asn
                340                 345                 350
Val Phe Val Trp Ile Gly Tyr Val Cys Ser Gly Ile Asn Pro Leu Val
                355                 360                 365
Tyr Thr Leu Phe Asn Lys Ile Tyr Arg Arg Ala Phe Ser Lys Tyr Leu
        370                 375                 380
Arg Cys Asp Tyr Lys Pro Asp Lys Lys Pro Pro Val Arg Gln Ile Pro
385                 390                 395                 400
Arg Val Ala Ala Thr Ala Leu Ser Gly Arg Glu Leu Asn Val Asn Ile
                405                 410                 415
Tyr Arg His Thr Asn Glu Arg Val Val Arg Lys Ala Asn Asp Thr Glu
                420                 425                 430
Pro Gly Ile Glu Met Gln Val Glu Asn Leu Glu Leu Pro Val Asn Pro
                435                 440                 445
Ser Asn Val Val Ser Glu Arg Ile Ser Ser Val
        450                 455

<210> SEQ ID NO 20
<211> LENGTH: 1380
<212> TYPE: DNA
<213> ORGANISM: MGI Transfected 293 Cells

<400> SEQUENCE: 20
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcaat gcgtggtcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga gaacgctccc     840
aaccccaatc cagatcagaa gccacgtcga aagaagaaag aaaagcggcc tagaggcacc     900
atgcaagcta tcaacaatga agagaaagct tccaaagtcc ttggcattgt attctttgtg     960
tttctgatca tgtggtgccc gttttttcatc accaatatcc tgtcggtgct tgtgggaag    1020
gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
```

-continued

```
tctaaatatt tgcgctgcga ttataagcca gacaaaaagc ctcctgttcg acagattcct   1200
agggttgctg ccactgcttt gtctgggagg gagctcaatg ttaacattta tcggcatacc   1260
aatgaacgtg tagttaggaa agctaatgac acagagcctg gcatagagat gcaggtagag   1320
aatttagagc tgccggtcaa tccctctaat gtggtcagcg agaggattag tagtgtgtaa   1380
```

<210> SEQ ID NO 21
<211> LENGTH: 459
<212> TYPE: PRT
<213> ORGANISM: MNV Transfected 293 Cells

<400> SEQUENCE: 21

```
Met Val Asn Leu Gly Thr Ala Val Arg Ser Leu Leu Val His Leu Ile
  1               5                  10                  15

Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
         35                  40                  45

Phe Pro Asp Gly Val Gln Asn Trp Pro Ala Leu Ser Ile Val Val Ile
     50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Met Arg Asn Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Asn Ala Pro Asn Pro Asn Pro Asp Gln Lys Pro
        275                 280                 285

Arg Arg Lys Lys Lys Glu Lys Arg Pro Arg Gly Thr Met Gln Ala Ile
    290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335
```

-continued

| | | | | | | | | | | | |
|---|---|---|---|---|---|---|---|---|---|---|---|
|Leu|Cys|Gly|Lys|Ala|Cys|Asn|Gln|Lys|Leu|Met|Glu|Lys|Leu|Leu|Asn|
| | | |340| | | |345| | | |350| | | | |
|Val|Phe|Val|Trp|Ile|Gly|Tyr|Val|Cys|Ser|Gly|Ile|Asn|Pro|Leu|Val|
| | | |355| | | |360| | | |365| | | | |
|Tyr|Thr|Leu|Phe|Asn|Lys|Ile|Tyr|Arg|Arg|Ala|Phe|Ser|Lys|Tyr|Leu|
| | | |370| | | |375| | | |380| | | | |
|Arg|Cys|Asp|Tyr|Lys|Pro|Asp|Lys|Lys|Pro|Pro|Val|Arg|Gln|Ile|Pro|
|385| | | |390| | | |395| | | |400| | | |
|Arg|Val|Ala|Ala|Thr|Ala|Leu|Ser|Gly|Arg|Glu|Leu|Asn|Val|Asn|Ile|
| | | | |405| | | |410| | | |415| | | |
|Tyr|Arg|His|Thr|Asn|Glu|Arg|Val|Val|Arg|Lys|Ala|Asn|Asp|Thr|Glu|
| | | |420| | | |425| | | |430| | | | |
|Pro|Gly|Ile|Glu|Met|Gln|Val|Glu|Asn|Leu|Glu|Leu|Pro|Val|Asn|Pro|
| | | |435| | | |440| | | |445| | | | |
|Ser|Asn|Val|Val|Ser|Glu|Arg|Ile|Ser|Ser|Val| | | | | |
| | | |450| | | |455| | | | | | | | |

<210> SEQ ID NO 22
<211> LENGTH: 1380
<212> TYPE: DNA
<213> ORGANISM: MNV Transfected 293 Cells

<400> SEQUENCE: 22

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcaat gcgtaatcct     480
gttgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga aacgctcccc     840
aaccccaatc cagatcagaa gccacgtcga aagaagaaag aaaagcggcc tagaggcacc     900
atgcaagcta tcaacaatga agaaagct tccaaagtcc ttggcattgt attctttgtg     960
tttctgatca tgtggtgccc gtttttcatc accaatatcc tgtcggtgct tgtgggaag    1020
gcctgtaacc aaaagctaat ggagaaactt ctcaatgtgt ttgtttggat ggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
agggttgctg ccactgcttt gtctgggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

-continued

```
<210> SEQ ID NO 23
<211> LENGTH: 459
<212> TYPE: PRT
<213> ORGANISM: IDV Transfected 293 Cells

<400> SEQUENCE: 23

Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
                20                  25                  30

Ile Val Thr Asp Thr Phe Asn Ser Ser Asp Gly Gly Arg Leu Phe Gln
            35                  40                  45

Phe Pro Asp Gly Val Gln Asn Trp Pro Ala Leu Ser Ile Val Val Ile
50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
130                 135                 140

His Leu Cys Ala Ile Ser Leu Asp Arg Tyr Val Ala Ile Arg Asp Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
        275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
        355                 360                 365

Tyr Thr Leu Phe Asn Lys Ile Tyr Arg Arg Ala Phe Ser Lys Tyr Leu
370                 375                 380
```

```
Arg Cys Asp Tyr Lys Pro Asp Lys Lys Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
    450                 455
```

<210> SEQ ID NO 24
<211> LENGTH: 1380
<212> TYPE: DNA
<213> ORGANISM: IDV Transfected 293 Cells

<400> SEQUENCE: 24

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcaat acgtgatcct     480
gttgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga gaacgctccc     840
aaccccaatc cagatcagaa gccacgtcga agaagaaaag aaaagcggcc tagaggcacc     900
atgcaagcta tcaacaatga aagaaagct tccaaagtcc ttggcattgt attctttgtg     960
tttctgatca tgtggtgccc gttttttcatc accaatatcc tgtcggtgct ttgtgggaag    1020
gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
agggttgctg ccactgcttt gtctgggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

<210> SEQ ID NO 25
<211> LENGTH: 459
<212> TYPE: PRT
<213> ORGANISM: IDI Transfected 293 Cells

<400> SEQUENCE: 25

```
Met Val Asn Leu Gly Thr Ala Val Arg Ser Leu Leu Val His Leu Ile
1               5                   10                  15
```

-continued

```
Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
             35                  40                  45

Phe Pro Asp Gly Val Gln Asn Trp Pro Ala Leu Ser Ile Val Val Ile
 50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
            115                 120                 125

Pro Val Trp Ile Ser Leu Asp Val Leu Phe Ser Thr Ala Ser Ile Met
130                 135                 140

His Leu Cys Ala Ile Ser Leu Asp Arg Tyr Val Ala Ile Arg Asp Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
            210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Arg Gly His Thr Glu Glu
                245                 250                 255

Glu Leu Arg Asn Ile Ser Leu Asn Phe Leu Lys Cys Cys Cys Lys Lys
                260                 265                 270

Gly Asp Glu Glu Asn Ala Pro Asn Pro Asn Pro Asp Gln Lys Pro
            275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
            420                 425                 430
```

```
Pro Gly Ile Glu Met Gln Val Glu Asn Leu Glu Leu Pro Val Asn Pro
        435                 440                 445

Ser Asn Val Val Ser Glu Arg Ile Ser Ser Val
    450                 455
```

<210> SEQ ID NO 26
<211> LENGTH: 1380
<212> TYPE: DNA
<213> ORGANISM: IDI Transfected 293 Cells

<400> SEQUENCE: 26

| | | | | | |
|---|---|---|---|---|---|
| atggtgaacc | tgggcactgc | ggtgcgctca | ctccttgtgc | acctaattgg | cctattggtt | 60 |
| tggcagttcg | atatttccat | aagtccagta | gcagctatag | taactgacac | ttttaattcc | 120 |
| tccgatggtg | gacgcttgtt | tcaattcccg | gacggggtac | aaaactggcc | agcactttca | 180 |
| atagtcgtga | ttataatcat | gacaataggg | gcaacattc | tcgttatcat | ggcagtaagc | 240 |
| atggagaaga | aactgcacaa | tgctaccaat | tatttcttaa | tgtccctagc | cattgctgat | 300 |
| atgctggtgg | gactacttgt | catgcccctg | tctctgcttg | caattcttta | tgattatgtc | 360 |
| tggcctttac | ctagatattt | gtccccgtc | tggatttcac | tagatgtgct | attttcaact | 420 |
| gcgtccatca | tgcacctctg | cgccatatcg | ctggaccggt | atgtagcaat | acgtgatcct | 480 |
| attgagcata | gccggttcaa | ttcgcggact | aaggccatca | tgaagattgc | catcgtttgg | 540 |
| gcaatatcaa | taggagtttc | agttcctatc | cctgtgattg | gactgaggga | cgaaagcaaa | 600 |
| gtgttcgtga | taatactac | ctgcgtgctc | aatgacccga | acttcgttct | catcgggtcc | 660 |
| ttcgtggcat | tcttcatccc | gttgacaatt | atggtgatca | cctacttctt | aacgatctac | 720 |
| gtcctacgcc | gtcaaaccct | gatgttactt | cgaggtcaca | ccgaggagga | actgcgtaat | 780 |
| atcagcctga | actttctaaa | gtgctgctgc | aagaagggtg | atgaggaaga | gaacgctccc | 840 |
| aaccccaatc | cagatcagaa | gccacgtcga | agaagaaag | aaaagcggcc | tagaggcacc | 900 |
| atgcaagcta | tcaacaatga | gaagaaagct | tccaaagtcc | ttggcattgt | attctttgtg | 960 |
| tttctgatca | tgtggtgccc | gttttttcatc | accaatatcc | tgtcggtgct | ttgtgggaag | 1020 |
| gcctgtaacc | aaaagctaat | ggagaaactt | ctcaatgtgt | ttgtttggat | tggctatgtg | 1080 |
| tgttcaggca | tcaatcctct | ggtgtacact | ctcttcaaca | aaatttaccg | aagggctttc | 1140 |
| tctaaatatt | tgcgctgcga | ttataagcca | gacaaaaagc | ctcctgttcg | acagattcct | 1200 |
| agggttgctg | ccactgcttt | gtctggagg | gagctcaatg | ttaacattta | tcggcatacc | 1260 |
| aatgaacgtg | tagttaggaa | agctaatgac | acagagcctg | gcatagagat | gcaggtagag | 1320 |
| aatttagagc | tgccggtcaa | tccctctaat | gtggtcagcg | agaggattag | tagtgtgtaa | 1380 |

<210> SEQ ID NO 27
<211> LENGTH: 459
<212> TYPE: PRT
<213> ORGANISM: IGV Transfected 293 Cells

<400> SEQUENCE: 27

```
Met Val Asn Leu Gly Thr Ala Val Arg Ser Leu Val His Leu Ile
 1               5                  10                  15

Gly Leu Leu Val Trp Gln Phe Asp Ile Ser Ile Ser Pro Val Ala Ala
                20                  25                  30

Ile Val Thr Asp Thr Phe Asn Ser Ser Asp Gly Gly Arg Leu Phe Gln
            35                  40                  45

Phe Pro Asp Gly Val Gln Asn Trp Pro Ala Leu Ser Ile Val Val Ile
        50                  55                  60
```

-continued

```
Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Val Met Pro Leu Ser Leu
            100                 105                 110

Leu Ala Ile Leu Tyr Asp Tyr Val Trp Pro Leu Pro Arg Tyr Leu Cys
            115                 120                 125

Pro Val Trp Ile Ser Leu Asp Val Leu Phe Ser Thr Ala Ser Ile Met
            130                 135                 140

His Leu Cys Ala Ile Ser Leu Asp Arg Tyr Val Ala Ile Arg Gly Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Asn Ala Pro Asn Pro Asn Pro Asp Gln Lys Pro
            275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
            325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
            405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
450                 455
```

<210> SEQ ID NO 28
<211> LENGTH: 1380
<212> TYPE: DNA
<213> ORGANISM: IGV Transfected 293 Cells

<400> SEQUENCE: 28

| | | | | |
|---|---|---|---|---|
| atggtgaacc tgggcactgc ggtgcgctca ctccttgtgc acctaattgg cctattggtt | 60 |
| tggcagttcg atatttccat aagtccagta gcagctatag taactgacac ttttaattcc | 120 |
| tccgatggtg gacgcttgtt tcaattcccg gacggggtac aaaactggcc agcactttca | 180 |
| atagtcgtga ttataatcat gacaataggg gcaacattc tcgttatcat ggcagtaagc | 240 |
| atggagaaga aactgcacaa tgctaccaat tatttcttaa tgtccctagc cattgctgat | 300 |
| atgctggtgg gactacttgt catgcccctg tctctgcttg caattcttta tgattatgtc | 360 |
| tggcctttac ctagatattt gtgccccgtc tggatttcac tagatgtgct attttcaact | 420 |
| gcgtccatca tgcacctctg cgccatatcg ctggaccggt atgtagcaat acgtggtcct | 480 |
| gttgagcata gccggttcaa ttcgcggact aaggccatca tgaagattgc catcgtttgg | 540 |
| gcaatatcaa taggagtttc agttcctatc cctgtgattg gactgaggga cgaaagcaaa | 600 |
| gtgttcgtga ataatactac ctgcgtgctc aatgacccga acttcgttct catcgggtcc | 660 |
| ttcgtggcat tcttcatccc gttgacaatt atggtgatca cctacttctt aacgatctac | 720 |
| gtcctacgcc gtcaaaccct gatgttactt cgaggtcaca ccgaggagga actgcgtaat | 780 |
| atcagcctga actttctaaa gtgctgctgc aagaagggtg atgaggaaga aacgctccc | 840 |
| aaccccaatc cagatcagaa gccacgtcga agaagaaag aaaagcggcc tagaggcacc | 900 |
| atgcaagcta tcaacaatga agaaaagct tccaaagtcc ttggcattgt attctttgtg | 960 |
| tttctgatca tgtggtgccc gtttttcatc accaatatcc tgtcggtgct ttgtgggaag | 1020 |
| gcctgtaacc aaaagctaat ggagaaactt ctcaatgtgt ttgtttggat tggctatgtg | 1080 |
| tgttcaggca tcaatcctct ggtgtacact ctcttcaaca aaatttaccg aagggctttc | 1140 |
| tctaaatatt tgcgctgcga ttataagcca gacaaaaagc tcctgttcg acagattcct | 1200 |
| agggttgctg ccactgcttt gtctgggagg gagctcaatg ttaacattta tcggcatacc | 1260 |
| aatgaacgtg tagttaggaa agctaatgac acagagcctg gcatagagat gcaggtagag | 1320 |
| aatttagagc tgccggtcaa tcctctaat gtggtcagcg agaggattag tagtgtgtaa | 1380 |

<210> SEQ ID NO 29
<211> LENGTH: 459
<212> TYPE: PRT
<213> ORGANISM: IGI Transfected 293 Cells

<400> SEQUENCE: 29

Met Val Asn Leu Gly Thr Ala Val Arg Ser Leu Leu Val His Leu Ile
1               5                   10                  15

Gly Leu Leu Val Trp Gln Phe Asp Ile Ser Ile Ser Pro Val Ala Ala
                20                  25                  30

Ile Val Thr Asp Thr Phe Asn Ser Ser Asp Gly Gly Arg Leu Phe Gln
            35                  40                  45

Phe Pro Asp Gly Val Gln Asn Trp Pro Ala Leu Ser Ile Val Val Ile
        50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

```
Ala Ile Ala Asp Met Leu Val Gly Leu Leu Val Met Pro Leu Ser Leu
         100                 105                 110

Leu Ala Ile Leu Tyr Asp Tyr Val Trp Pro Leu Pro Arg Tyr Leu Cys
         115                 120                 125

Pro Val Trp Ile Ser Leu Asp Val Leu Phe Ser Thr Ala Ser Ile Met
         130                 135                 140

His Leu Cys Ala Ile Ser Leu Asp Arg Tyr Val Ala Ile Arg Gly Pro
145                 150                 155                 160

Ile Glu His Ser Arg Phe Asn Ser Arg Thr Lys Ala Ile Met Lys Ile
                 165                 170                 175

Ala Ile Val Trp Ala Ile Ser Ile Gly Val Ser Val Pro Ile Pro Val
                 180                 185                 190

Ile Gly Leu Arg Asp Glu Ser Lys Val Phe Val Asn Thr Thr Cys
         195                 200                 205

Val Leu Asn Asp Pro Asn Phe Val Leu Ile Gly Ser Phe Val Ala Phe
         210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                 245                 250                 255

Glu Leu Arg Asn Ile Ser Leu Asn Phe Leu Lys Cys Cys Cys Lys Lys
                 260                 265                 270

Gly Asp Glu Glu Glu Asn Ala Pro Asn Pro Asn Pro Asp Gln Lys Pro
             275                 280                 285

Arg Arg Lys Lys Lys Glu Lys Arg Pro Arg Gly Thr Met Gln Ala Ile
         290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                 325                 330                 335

Leu Cys Gly Lys Ala Cys Asn Gln Lys Leu Met Glu Lys Leu Leu Asn
                 340                 345                 350

Val Phe Val Trp Ile Gly Tyr Val Cys Ser Gly Ile Asn Pro Leu Val
                 355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                 405                 410                 415

Tyr Arg His Thr Asn Glu Arg Val Val Arg Lys Ala Asn Asp Thr Glu
                 420                 425                 430

Pro Gly Ile Glu Met Gln Val Glu Asn Leu Glu Leu Pro Val Asn Pro
             435                 440                 445

Ser Asn Val Val Ser Glu Arg Ile Ser Ser Val
    450                 455

<210> SEQ ID NO 30
<211> LENGTH: 1380
<212> TYPE: DNA
<213> ORGANISM: IGI Transfected 293 Cells

<400> SEQUENCE: 30
atggtgaacc tgggcactgc ggtgcgctca ctccttgtgc acctaattgg cctattggtt      60
```

-continued

```
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
tggcctttac ctagatattt gtgccccgtc tggatttcac tagatgtgct atttttcaact   420 gcgtccatca tgcacctctg cgccatatcg ctggaccggt atgtagcaat acgtggtcct    480
attgagcata gccggttcaa ttcgcggact aaggccatca tgaagattgc catcgtttgg    540
gcaatatcaa taggagtttc agttcctatc cctgtgattg gactgaggga cgaaagcaaa    600
gtgttcgtga ataatactac ctgcgtgctc aatgacccga acttcgttct catcgggtcc    660
ttcgtggcat tcttcatccc gttgacaatt atggtgatca cctacttctt aacgatctac    720
gtcctacgcc gtcaaaccct gatgttactt cgaggtcaca ccgaggagga actgcgtaat    780
atcagcctga actttctaaa gtgctgctgc aagaagggtg atgaggaaga gaacgctccc    840
aaccccaatc cagatcagaa gccacgtcga agaagaaag aaaagcggcc tagaggcacc     900
atgcaagcta tcaacaatga gaagaaagct tccaaagtcc ttggcattgt attctttgtg    960
tttctgatca tgtggtgccc gttttcatc accaatatcc tgtcggtgct ttgtgggaag    1020
gcctgtaacc aaaagctaat ggagaaactt ctcaatgtgt ttgtttggat ggctatgtg    1080 tgttcaggca tcaatcctct ggtgtacact ctcttcaaca aaatttaccg aagggctttc   1140
tctaaatatt tgcgctgcga ttataagcca gacaaaaagc ctcctgttcg acagattcct   1200
agggttgctg ccactgcttt gtctggggag gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

<210> SEQ ID NO 31
<211> LENGTH: 459
<212> TYPE: PRT
<213> ORGANISM: INI Transfected 293 Cells

<400> SEQUENCE: 31

```
Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
         35                  40                  45

Phe Pro Asp Gly Val Gln Asn Trp Pro Ala Leu Ser Ile Val Val Ile
     50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140
```

```
His Leu Cys Ala Ile Ser Leu Asp Arg Tyr Val Ala Ile Arg Asn Pro
145                 150                 155                 160

Ile Glu His Ser Arg Phe Asn Ser Arg Thr Lys Ala Ile Met Lys Ile
            165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
            245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
            275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
            325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
            405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
    450                 455

<210> SEQ ID NO 32
<211> LENGTH: 1380
<212> TYPE: DNA
<213> ORGANISM: INI Transfected 293 Cells

<400> SEQUENCE: 32
atggtgaacc tgggcactgc ggtgcgctca ctccttgtgc acctaattgg cctattggtt      60
tggcagttcg atatttccat aagtccagta gcagctatag taactgacac ttttaattcc    120
tccgatggtg gacgcttgtt tcaattcccg gacggggtac aaaactggcc agcactttca    180
atagtcgtga ttataatcat gacaataggg ggcaacattc tcgttatcat ggcagtaagc    240
atggagaaga aactgcacaa tgctaccaat tatttcttaa tgtccctagc cattgctgat    300
atgctggtgg gactacttgt catgcccctg tctctgcttg caattcttta tgattatgtc    360
```

-continued

```
tggcctttac ctagatattt gtgccccgtc tggatttcac tagatgtgct attttcaact      420
gcgtccatca tgcacctctg cgccatatcg ctggaccggt atgtagcaat acgtaatcct      480
attgagcata gccggttcaa ttcgcggact aaggccatca tgaagattgc catcgtttgg      540
gcaatatcaa taggagtttc agttcctatc cctgtgattg gactgaggga cgaaagcaaa      600
gtgttcgtga ataatactac ctgcgtgctc aatgacccga acttcgttct catcgggtcc      660
ttcgtggcat tcttcatccc gttgacaatt atggtgatca cctacttctt aacgatctac      720
gtcctacgcc gtcaaaccct gatgttactt cgaggtcaca ccgaggagga actgcgtaat      780
atcagcctga actttctaaa gtgctgctgc aagaagggtg atgaggaaga gaacgctccc      840
aaccccaatc cagatcagaa gccacgtcga agaagaaag aaaagcggcc tagaggcacc       900
atgcaagcta tcaacaatga aagaaagct tccaaagtcc ttggcattgt attctttgtg       960
tttctgatca tgtggtgccc gttttcatc accaatatcc gtcggtgct ttgtgggaag       1020
gcctgtaacc aaaagctaat ggagaaactt ctcaatgtgt ttgtttggat tggctatgtg     1080
tgttcaggca tcaatcctct ggtgtacact ctcttcaaca aaatttaccg aagggctttc     1140
tctaaatatt tgcgctgcga ttataagcca gacaaaaagc ctcctgttcg acagattcct     1200
agggttgctg ccactgcttt gtctgggagg gagctcaatg ttaacattta tcggcatacc     1260
aatgaacgtg tagttaggaa agctaatgac acagagcctg gcatagagat gcaggtagag     1320
aatttagagc tgccggtcaa tccctctaat gtggtcagcg agaggattag tagtgtgtaa     1380
```

<210> SEQ ID NO 33
<211> LENGTH: 459
<212> TYPE: PRT
<213> ORGANISM: VDI Transfected 293 Cells

<400> SEQUENCE: 33

```
Met Val Asn Leu Gly Thr Ala Val Arg Ser Leu Val His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Val Arg Asp Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190
```

```
Ile Gly Leu Arg Asp Glu Ser Lys Val Phe Val Asn Asn Thr Thr Cys
            195                 200                 205
Val Leu Asn Asp Pro Asn Phe Val Leu Ile Gly Ser Phe Val Ala Phe
        210                 215                 220
Phe Ile Pro Leu Thr Ile Met Val Ile Thr Tyr Phe Leu Thr Ile Tyr
225                 230                 235                 240
Val Leu Arg Arg Gln Thr Leu Met Leu Leu Arg Gly His Thr Glu Glu
                245                 250                 255
Glu Leu Arg Asn Ile Ser Leu Asn Phe Leu Lys Cys Cys Cys Lys Lys
            260                 265                 270
Gly Asp Glu Glu Glu Asn Ala Pro Asn Pro Asn Pro Asp Gln Lys Pro
        275                 280                 285
Arg Arg Lys Lys Lys Glu Lys Arg Pro Arg Gly Thr Met Gln Ala Ile
290                 295                 300
Asn Asn Glu Lys Lys Ala Ser Lys Val Leu Gly Ile Val Phe Phe Val
305                 310                 315                 320
Phe Leu Ile Met Trp Cys Pro Phe Phe Ile Thr Asn Ile Leu Ser Val
                325                 330                 335
Leu Cys Gly Lys Ala Cys Asn Gln Lys Leu Met Glu Lys Leu Leu Asn
            340                 345                 350
Val Phe Val Trp Ile Gly Tyr Val Cys Ser Gly Ile Asn Pro Leu Val
        355                 360                 365
Tyr Thr Leu Phe Asn Lys Ile Tyr Arg Arg Ala Phe Ser Lys Tyr Leu
370                 375                 380
Arg Cys Asp Tyr Lys Pro Asp Lys Lys Pro Pro Val Arg Gln Ile Pro
385                 390                 395                 400
Arg Val Ala Ala Thr Ala Leu Ser Gly Arg Glu Leu Asn Val Asn Ile
                405                 410                 415
Tyr Arg His Thr Asn Glu Arg Val Val Arg Lys Ala Asn Asp Thr Glu
            420                 425                 430
Pro Gly Ile Glu Met Gln Val Glu Asn Leu Glu Leu Pro Val Asn Pro
        435                 440                 445
Ser Asn Val Val Ser Glu Arg Ile Ser Ser Val
450                 455
```

<210> SEQ ID NO 34
<211> LENGTH: 1380
<212> TYPE: DNA
<213> ORGANISM: VDI Transfected 293 Cells

<400> SEQUENCE: 34

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacgggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcagt acgtgatcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
```

-continued

```
gtgttcgtga ataatactac ctgcgtgctc aatgacccga acttcgttct catcgggtcc    660
ttcgtggcat tcttcatccc gttgacaatt atggtgatca cctacttctt aacgatctac    720
gtcctacgcc gtcaaaccct gatgttactt cgaggtcaca ccgaggagga actgcgtaat    780
atcagcctga actttctaaa gtgctgctgc aagaagggtg atgaggaaga gaacgctccc    840
aaccccaatc cagatcagaa gccacgtcga aagaagaaag aaaagcggcc tagaggcacc    900
atgcaagcta tcaacaatga gaagaaagct tccaaagtcc ttggcattgt attctttgtg    960
tttctgatca tgtggtgccc gtttttcatc accaatatcc tgtcggtgct ttgtgggaag   1020
gcctgtaacc aaaagctaat ggagaaactt ctcaatgtgt ttgtttggat tggctatgtg   1080
tgttcaggca tcaatcctct ggtgtacact ctcttcaaca aaatttaccg aagggctttc   1140
tctaaatatt tgcgctgcga ttataagcca gacaaaaagc ctcctgttcg acagattcct   1200
agggttgctg ccactgcttt gtctgggagg gagctcaatg ttaacattta tcggcatacc   1260
aatgaacgtg tagttaggaa agctaatgac acagagcctg gcatagagat gcaggtagag   1320
aatttagagc tgccggtcaa tccctctaat gtggtcagcg agaggattag tagtgtgtaa   1380
```

```

<210> SEQ ID NO 35
<211> LENGTH: 459
<212> TYPE: PRT
<213> ORGANISM: VGV Transfected 293 Cells

<400> SEQUENCE: 35

Met Val Asn Leu Gly Thr Ala Val Arg Ser Leu Leu Val His Leu Ile
 1               5                   10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Val Arg Gly Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240
```

```
Val Leu Arg Arg Gln Thr Leu Met Leu Arg Gly His Thr Glu Glu
                245                 250                 255

Glu Leu Arg Asn Ile Ser Leu Asn Phe Leu Lys Cys Cys Lys Lys
                260                 265                 270

Gly Asp Glu Glu Asn Ala Pro Asn Pro Asn Pro Asp Gln Lys Pro
                275                 280                 285

Arg Arg Lys Lys Lys Glu Lys Arg Pro Arg Gly Thr Met Gln Ala Ile
                290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
                340                 345                 350

Val Phe Val Trp Ile Gly Tyr Val Cys Ser Gly Ile Asn Pro Leu Val
                355                 360                 365

Tyr Thr Leu Phe Asn Lys Ile Tyr Arg Arg Ala Phe Ser Lys Tyr Leu
                370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
                420                 425                 430

Pro Gly Ile Glu Met Gln Val Glu Asn Leu Glu Leu Pro Val Asn Pro
                435                 440                 445

Ser Asn Val Val Ser Glu Arg Ile Ser Ser Val
        450                 455

<210> SEQ ID NO 36
<211> LENGTH: 1380
<212> TYPE: DNA
<213> ORGANISM: VGV Transfected 293 Cells

<400> SEQUENCE: 36
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcagt acgtggtcct     480
gttgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga gaacgctccc     840
aaccccaatc cagatcagaa gccacgtcga aagaagaaag aaaagcggcc tagaggcacc     900
```

-continued

```
atgcaagcta tcaacaatga aagaaagct tccaaagtcc ttggcattgt attctttgtg      960
tttctgatca tgtggtgccc gttttcatc accaatatcc tgtcggtgct tgtgggaag      1020 gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
tctaaatatt tgcgctgcga ttataagcca gacaaaaagc tcctgttcg acagattcct    1200 agggttgctg ccactgcttt gtctgggagg gagctcaatg ttaacattta tcggcatacc    1260
aatgaacgtg tagttaggaa agctaatgac acagagcctg catagagat gcaggtagag     1320 aatttagagc tgccggtcaa tccctctaat gtggtcagcg agaggattag tagtgtgtaa   1380
```

<210> SEQ ID NO 37
<211> LENGTH: 459
<212> TYPE: PRT
<213> ORGANISM: VGI Transfected 293 Cells

<400> SEQUENCE: 37

```
Met Val Asn Leu Gly Thr Ala Val Arg Ser Leu Leu Val His Leu Ile
  1               5                  10                  15

Gly Leu Leu Val Trp Gln Phe Asp Ile Ser Ile Ser Pro Val Ala Ala
              20                  25                  30

Ile Val Thr Asp Thr Phe Asn Ser Ser Asp Gly Gly Arg Leu Phe Gln
          35                  40                  45

Phe Pro Asp Gly Val Gln Asn Trp Pro Ala Leu Ser Ile Val Val Ile
      50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Val Arg Gly Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
        275                 280                 285
```

```
Arg Arg Lys Lys Lys Glu Lys Arg Pro Arg Gly Thr Met Gln Ala Ile
        290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
        370                 375                 380

Arg Cys Asp Tyr Lys Pro Asp Lys Lys Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
        450                 455

<210> SEQ ID NO 38
<211> LENGTH: 1380
<212> TYPE: DNA
<213> ORGANISM: VGI Transfected 293 Cells

<400> SEQUENCE: 38
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgccccgtc tggatttcac tagatgtgct attttcaact     420
gcgtccatca tgcacctctg cgccatatcg ctggaccggt atgtagcagt acgtggtcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga aacgctcccc     840
aaccccaatc cagatcagaa gccacgtcga aagaagaaag aaaagcggcc tagaggcacc     900
atgcaagcta tcaacaatga agagaaagct tccaaagtcc ttggcattgt attctttgtg     960
tttctgatca tgtggtgccc gttttttcatc accaatatcc tgtcggtgct tgtgggaag    1020 gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
```

-continued

```
tctaaatatt tgcgctgcga ttataagcca gacaaaaagc ctcctgttcg acagattcct    1200
agggttgctg ccactgcttt gtctgggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

<210> SEQ ID NO 39
<211> LENGTH: 459
<212> TYPE: PRT
<213> ORGANISM: VNI Transfected 293 Cells

<400> SEQUENCE: 39

```
Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
         35                  40                  45

Phe Pro Asp Gly Val Gln Asn Trp Pro Ala Leu Ser Ile Val Val Ile
     50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
                 85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Val Arg Asn Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Asn Ala Pro Asn Pro Asn Pro Asp Gln Lys Pro
        275                 280                 285

Arg Arg Lys Lys Lys Glu Lys Arg Pro Arg Gly Thr Met Gln Ala Ile
    290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335
```

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
            370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Val Arg Lys Ala Asn Asp Thr Glu
                420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
            450                 455

<210> SEQ ID NO 40
<211> LENGTH: 1380
<212> TYPE: DNA
<213> ORGANISM: VNI Transfected 293 Cells

<400> SEQUENCE: 40

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg acgggqtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattctttta tgattatgtc     360
tggcctttac ctagatattt gtgccccgtc tggatttcac tagatgtgct atttttcaact     420
gcgtccatca tgcacctctg cgccatatcg ctggaccggt atgtagcagt acgtaatcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga acttcgttct catcgggtcc     660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga aacgctccc     840
aaccccaatc cagatcagaa gccacgtcga agaagaaag aaaagcggcc tagaggcacc     900
atgcaagcta tcaacaatga aagaaaagct tccaaagtcc ttggcattgt attctttgtg     960
tttctgatca tgtggtgccc gttttttcatc accaatatcc tgtcggtgct ttgtgggaag    1020
gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
agggttgctg ccactgcttt gtctggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

```
<210> SEQ ID NO 41
<211> LENGTH: 459
<212> TYPE: PRT
<213> ORGANISM: MSV Transfected 293 Cells

<400> SEQUENCE: 41

Met Val Asn Leu Gly Thr Ala Val Arg Ser Leu Leu Val His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Met Arg Ser Pro
145                 150                 155                 160

Val Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
        195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Arg Asn Ile Ser Leu Asn Phe Leu Lys Cys Cys Cys Lys Lys
            260                 265                 270

Gly Asp Glu Glu Glu Asn Ala Pro Asn Pro Asn Pro Asp Gln Lys Pro
        275                 280                 285

Arg Arg Lys Lys Lys Glu Lys Arg Pro Arg Gly Thr Met Gln Ala Ile
    290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
                325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
        355                 360                 365

Tyr Thr Leu Phe Asn Lys Ile Tyr Arg Arg Ala Phe Ser Lys Tyr Leu
    370                 375                 380
```

Arg Cys Asp Tyr Lys Pro Asp Lys Lys Pro Val Arg Gln Ile Pro
385                 390                 395                 400

Arg Val Ala Ala Thr Ala Leu Ser Gly Arg Glu Leu Asn Val Asn Ile
                405                 410                 415

Tyr Arg His Thr Asn Glu Arg Val Arg Lys Ala Asn Asp Thr Glu
            420                 425                 430

Pro Gly Ile Glu Met Gln Val Glu Asn Leu Glu Leu Pro Val Asn Pro
            435                 440                 445

Ser Asn Val Val Ser Glu Arg Ile Ser Ser Val
    450                 455

<210> SEQ ID NO 42
<211> LENGTH: 1380
<212> TYPE: DNA
<213> ORGANISM: MSV Transfected 293 Cells

<400> SEQUENCE: 42

| | | |
|---|---|---|
| atggtgaacc tgggcactgc ggtgcgctca ctccttgtgc acctaattgg cctattggtt | 60 |
| tggcagttcg atatttccat aagtccagta gcagctatag taactgacac ttttaattcc | 120 |
| tccgatggtg gacgcttgtt tcaattcccg gacggggtac aaaactggcc agcactttca | 180 |
| atagtcgtga ttataatcat gacaataggg ggcaacattc tcgttatcat ggcagtaagc | 240 |
| atggagaaga aactgcacaa tgctaccaat tatttcttaa tgtccctagc cattgctgat | 300 |
| atgctggtgg gactacttgt catgccctg tctctgcttg caattcttta tgattatgtc | 360 |
| tggcctttac ctagatattt gtgccccgtc tggatttcac tagatgtgct attttcaact | 420 |
| gcgtccatca tgcacctctg cgccatatcg ctggaccggt atgtagcaat gcgtagtcct | 480 |
| gttgagcata gccggttcaa ttcgcggact aaggccatca tgaagattgc catcgtttgg | 540 |
| gcaatatcaa taggagtttc agttcctatc cctgtgattg gactgaggga cgaaagcaaa | 600 |
| gtgttcgtga ataatactac ctgcgtgctc aatgacccga cttcgttcct catcgggtcc | 660 |
| ttcgtggcat tcttcatccc gttgacaatt atggtgatca cctacttctt aacgatctac | 720 |
| gtcctacgcc gtcaaaccct gatgttactt cgaggtcaca ccgaggagga actgcgtaat | 780 |
| atcagcctga ctttctaaa gtgctgctgc aagaagggtg atgaggaaga gaacgctccc | 840 |
| aaccccaatc cagatcagaa gccacgtcga agaagaaag aaaagcggcc tagaggcacc | 900 |
| atgcaagcta tcaacaatga aagaaagct tccaaagtcc ttggcattgt attctttgtg | 960 |
| tttctgatca tgtggtgccc gttttttcatc accaatatcc tgtcggtgct tgtgggaag | 1020 |
| gcctgtaacc aaaagctaat ggagaaactt ctcaatgtgt ttgttggat tggctatgtg | 1080 |
| tgttcaggca tcaatcctct ggtgtacact ctcttcaaca aaatttaccg aagggctttc | 1140 |
| tctaaatatt tgcgctgcga ttataagcca gacaaaaagc ctcctgttcg acagattcct | 1200 |
| agggttgctg ccactgcttt gtctgggagg gagctcaatg ttaacattta tcggcatacc | 1260 |
| aatgaacgtg tagttaggaa agctaatgac acagagcctg gcatagagat gcaggtagag | 1320 |
| aatttagagc tgccggtcaa tccctctaat gtggtcagcg agaggattag tagtgtgtaa | 1380 |

<210> SEQ ID NO 43
<211> LENGTH: 459
<212> TYPE: PRT
<213> ORGANISM: MSI Transfected 293 Cells

<400> SEQUENCE: 43

Met Val Asn Leu Gly Thr Ala Val Arg Ser Leu Leu Val His Leu Ile
1               5                   10                  15

-continued

```
Gly Leu Leu Val Trp Gln Phe Asp Ile Ser Ile Ser Pro Val Ala Ala
             20                  25                  30

Ile Val Thr Asp Thr Phe Asn Ser Ser Asp Gly Gly Arg Leu Phe Gln
             35                  40                  45

Phe Pro Asp Gly Val Gln Asn Trp Pro Ala Leu Ser Ile Val Val Ile
 50                  55                  60

Ile Ile Met Thr Ile Gly Gly Asn Ile Leu Val Ile Met Ala Val Ser
 65                  70                  75                  80

Met Glu Lys Lys Leu His Asn Ala Thr Asn Tyr Phe Leu Met Ser Leu
             85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
            115                 120                 125

Pro Val Trp Ile Ser Leu Asp Val Leu Phe Ser Thr Ala Ser Ile Met
130                 135                 140

His Leu Cys Ala Ile Ser Leu Asp Arg Tyr Val Ala Met Arg Ser Pro
145                 150                 155                 160

Ile Glu His Ser Arg Phe Asn Ser Arg Thr Lys Ala Ile Met Lys Ile
            165                 170                 175

Ala Ile Val Trp Ala Ile Ser Ile Gly Val Ser Val Pro Ile Pro Val
            180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
            210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Arg Gly His Thr Glu Glu
            245                 250                 255

Glu Leu Arg Asn Ile Ser Leu Asn Phe Leu Lys Cys Cys Cys Lys Lys
            260                 265                 270

Gly Asp Glu Glu Asn Ala Pro Asn Pro Asn Pro Asp Gln Lys Pro
            275                 280                 285

Arg Arg Lys Lys Lys Glu Lys Arg Pro Arg Gly Thr Met Gln Ala Ile
290                 295                 300

Asn Asn Glu Lys Lys Ala Ser Lys Val Leu Gly Ile Val Phe Phe Val
305                 310                 315                 320

Phe Leu Ile Met Trp Cys Pro Phe Phe Ile Thr Asn Ile Leu Ser Val
            325                 330                 335

Leu Cys Gly Lys Ala Cys Asn Gln Lys Leu Met Glu Lys Leu Leu Asn
            340                 345                 350

Val Phe Val Trp Ile Gly Tyr Val Cys Ser Gly Ile Asn Pro Leu Val
            355                 360                 365

Tyr Thr Leu Phe Asn Lys Ile Tyr Arg Arg Ala Phe Ser Lys Tyr Leu
370                 375                 380

Arg Cys Asp Tyr Lys Pro Asp Lys Lys Pro Pro Val Arg Gln Ile Pro
385                 390                 395                 400

Arg Val Ala Ala Thr Ala Leu Ser Gly Arg Glu Leu Asn Val Asn Ile
            405                 410                 415

Tyr Arg His Thr Asn Glu Arg Val Val Arg Lys Ala Asn Asp Thr Glu
            420                 425                 430
```

```
Pro Gly Ile Glu Met Gln Val Glu Asn Leu Glu Leu Pro Val Asn Pro
        435                 440                 445
Ser Asn Val Val Ser Glu Arg Ile Ser Ser Val
    450                 455
```

<210> SEQ ID NO 44
<211> LENGTH: 1380
<212> TYPE: DNA
<213> ORGANISM: MSI Transfected 293 Cells

<400> SEQUENCE: 44

```
atggtgaacc tgggcactgc ggtgcgctca ctccttgtgc acctaattgg cctattggtt      60
tggcagttcg atatttccat aagtccagta gcagctatag taactgacac ttttaattcc     120
tccgatggtg gacgcttgtt tcaattcccg gacggggtac aaaactggcc agcactttca     180
atagtcgtga ttataatcat gacaataggg ggcaacattc tcgttatcat ggcagtaagc     240
atggagaaga aactgcacaa tgctaccaat tatttcttaa tgtccctagc cattgctgat     300
atgctggtgg gactacttgt catgcccctg tctctgcttg caattcttta tgattatgtc     360
tggcctttac ctagatattt gtgcccgtc tggatttcac tagatgtgct attttcaact     420
gcgtccatca tgcacctctg cgccatatcg ctggaccggt atgtagcaat gcgtagtcct     480
attgagcata gccggttcaa ttcgcggact aaggccatca tgaagattgc catcgtttgg     540
gcaatatcaa taggagtttc agttcctatc cctgtgattg gactgaggga cgaaagcaaa     600
gtgttcgtga ataatactac ctgcgtgctc aatgacccga cttcgttct catcgggtcc      660
ttcgtggcat tcttcatccc gttgacaatt atggtgatca cctacttctt aacgatctac     720
gtcctacgcc gtcaaaccct gatgttactt cgaggtcaca ccgaggagga actgcgtaat     780
atcagcctga actttctaaa gtgctgctgc aagaagggtg atgaggaaga gaacgctccc     840
aaccccaatc cagatcagaa gccacgtcga aagaagaaag aaaagcggcc tagaggcacc     900
atgcaagcta tcaacaatga gaagaaagct tccaaagtcc ttggcattgt attctttgtg     960
tttctgatca tgtggtgccc gttttcatc accaatatcc tgtcggtgct ttgtgggaag    1020
gcctgtaacc aaaagctaat ggagaaactt ctcaatgtgt ttgtttggat tggctatgtg    1080
tgttcaggca tcaatcctct ggtgtacact ctcttcaaca aaatttaccg aagggctttc    1140
tctaaatatt tgcgctgcga ttataagcca gacaaaaagc ctcctgttcg acagattcct    1200
agggttgctg ccactgcttt gtctggagg gagctcaatg ttaacattta tcggcatacc    1260
aatgaacgtg tagttaggaa agctaatgac acagagcctg gcatagagat gcaggtagag    1320
aatttagagc tgccggtcaa tccctctaat gtggtcagcg agaggattag tagtgtgtaa    1380
```

ISOFORMS OF MOUSE SEROTONIN 5-HT2C RECEPTOR

CROSS REFERENCE TO RELATED APPLICATIONS

The present application claims priority of U.S. provisional application Serial No. 60/124,439, filed Mar. 15, 1999.

BACKGROUND OF THE INVENTION

Serotonin is a neuromodulator capable of inducing and modulating a wide variety of behavioral functions such as sleep, appetite, locomotion, sexual activity and vascular contraction. It is accepted that serotonin activity is mediated by its interaction with receptors, designated serotoninergic receptors of 5-HT (for 5-hydroxytryptamine) receptors. Molecular biology studies as well as pharmacological studies have revealed the existence of a large number of subtypes of 5-HT receptors. The 5-HT receptors which have been described to date belong either to the family of receptors associated with ion channels (5-HT3 receptors), or to the family of receptors which interact with G proteins and which possess seven transmembrane domains. Moreover, analysis of the amino acid sequences has shown that the 5-HT receptors which interact with G proteins may be subdivided into six distinct groups: 5-HT1 receptors, comprising the mammalian subtypes 5-HT1a, 5-HT1b, 5-HT1d, 5-HT1e and 5-HT1f, as well as three Drosophila 5-HT receptors; 5-HT2 receptors comprising three subtypes, 5-HT2a, 5-HT2b and 5-HT2c; 5-HT4 receptor; 5-HT5 receptor; 5-HT6 receptor; and 5-HT7 receptor.

Drugs with affinity for 5-HT2 receptors are used to treat schizophrenia, Parkinsonism, and anxiety disorders. The 5-HT2c receptor subtype has been particularly interesting to investigators searching for the molecular bases of neuropsychiatric disorders. The 5-HT2c receptor is widely expressed in the brain where it is involved in regulating endocrine responses. Particular responses include the production and secretion of adrenocorticotropic hormone, oxytocin and prolactin. Genes for mouse, rat and human (Saltzman et al., *Biochem. Biophys. Res. Commun.* 181:1469, 1991) 5-HT2c receptors have been cloned. Burns et al., *Nature* vol. 387 15 May 1997 pp. 303–308 describes rat 5-HT2c receptor isoforms resulting from RNA editing events involving transcripts encodong the serotonin receptor. The functional state of 5-HT2c receptors in normal controls and various patient groups has been studied in vivo by administering 1-(3-chlorophenyl)piperazine (mCPP), a non-selective 5-HT2c agonist, and measuring hormonal and psychological responses. In alcoholism, panic disorder, seasonal affective disorder and obsessive-compulsive disorder, mCPP has been shown to induce different hormonal and psychological responses in patients and controls.

SUMMARY OF THE INVENTION

The invention includes mouse serotonin 5-HT2c receptor isoforms having amino acid replacements at one or more positions of the previously known mouse serotonin 5-HT2c receptor polypeptide sequence, specifically at one or more of positions 157, 159 and 161. The invention also includes isolated or purified isoforms, DNA encoding the isoforms, antibodies with specific binding to the receptor isoforms, assays for detecting the receptor isoforms, and expression vectors encoding the receptor isoforms.

DETAILED DESCRIPTION OF THE INVENTION

The invention includes an isolated polypeptide comprising a sequence selected from the group consisting of (a) SEQ ID No. 3, (b) SEQ ID No. 5, (c) SEQ ID No. 7, (d) SEQ ID No. 9, (e) SEQ ID No. 11, and (f) fragments of (a), (b), (c), (d), and (e) wherein the polypeptide has serotonin activity. These polypeptides are mouse serotonin 5-HT2c receptor isoforms having amino acid replacements at one or more positions of the previously known mouse serotonin 5-HT2c receptor polypeptide sequence, specifically at one or more of positions 157, 159 and 161.

The polypeptides are useful for identifying ligands which bind with the serotonin 5-HT2c receptor and modulators of the serotonin 5-HT2c, and for identifying drugs with affinity for 5-HT2 receptors which are used to treat schizophrenia, Parkinsonism, and anxiety disorders.

The invention also includes a method for identifying modulators of a polypeptide comprising a sequence selected from the group consisting of (a) SEQ ID No. 3, (b) SEQ ID No. 5, (c) SEQ ID No. 7, (d) SEQ ID No. 9, (e) SEQ ID No. 11, and (f) fragments of (a), (b), (c), (d), and (e), comprising contacting in the presence of 5-HTa molecule or a mixture containing different molecules with a recombinant cell expressing at its surface a polypeptide of claim 1, under conditions permitting interaction between the polypeptide and 5-HT, and detecting molecules capable of modulating the activity of the polypeptide in the presence or absence of 5HT.

The invention also includes isloated nucleotide sequences coding for a polypeptide comprising a sequence selected from the group consisting of (a) SEQ ID No. 3, (b) SEQ ID No. 5, (c) SEQ ID No. 7, (d) SEQ ID No. 9, (e) SEQ ID No. 11, and (f) fragments of (a), (b), (c), (d), and (e), or the complementary strand, including such nucleotide sequences consisting of genomic sequences, cDNA sequences, RNA sequences, synthetic sequences and semi-synthetic sequences. Also within the the invention are such sequences placed under the control of signals permitting expression of the polypeptide in a host cell.

The invention also includes recombinant cells comprising nucleotide sequences of the invention, including eukaryotic and prokaryotic cells, and vectors for transforming the cells.

The invention also includes mammalian cell membranes comprising a polypeptide sequence selected from the group consisting of (a) SEQ ID No. 3, (b) SEQ ID No. 5, (c) SEQ ID No. 7, (d) SEQ ID No. 9, (e) SEQ ID No. 11, and (f) fragments of (a), (b), (c), (d), and (e) wherein the polypeptide has serotonin receptor activity. Optionally, the mammalian cell membranes are free of other receptor proteins. The mammalian cell membranes may be prepared from mammalian cells containing cDNA which encodes any of the polypeptides. The mammalian cells are transfected with recombinant DNA comprising vector DNA and cDNA which encode the polypeptides.

The invention also includes a method for identifying ligands of a polypeptide comprising a sequence selected from the group consisting of (a) SEQ ID No. 3, (b) SEQ ID No. 5, (c) SEQ ID No. 7, (d) SEQ ID No. 9, (e) SEQ ID No. 11, and (f) fragments of (a), (b), (c), (d), and (e), comprising contacting a molecule or a mixture containing different molecules with a recombinant cell expressing at its surface one of the polypeptides, under conditions permitting interaction between the polypeptide and the molecule, and detecting molecules bound to the polypeptide.

The invention also includes a method for identifying modulators of a polypeptide comprising a sequence selected from the group consisting of (a) SEQ ID No. 3, (b) SEQ ID No. 5, (c) SEQ ID No. 7, (d) SEQ ID No. 9, (e) SEQ ID No. 11, and (f) fragments of (a), (b), (c), (d), and (e), comprising contacting in the presence of 5-HTa molecule or a mixture containing different molecules with a recombinant cell expressing at its surface a polypeptide of claim 1, under conditions permitting interaction between the polypeptide and 5-HT, and detecting molecules capable of modulating the activity of the polypeptide in the presence or absence of 5HT.

The present invention further includes antibodies specific for the serotonin receptor isoform proteins of the invention which do not bind to the receptor as described by Yu et al. in GenBank X72230.

The term "isolated" refers to material that is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The mouse serotonin 5-HT2c subtype cDNA isoforms were subcloned into the expression vector pE3 which is modified as described below from pCEP4 (Invitrogen, Carlsbad, Calif.). Transient expression in HEK293e cells (Invitrogen, Carlsbad, Calif.) was accomplished by transfection of the cloned receptor cDNAs under the control of a CMV promoter into mammalian cells (e.g., HEK293e cells). Membranes prepared from the transfected cells are utilized for the determination of binding affinity, selectivity and specificity of the receptors for various ligands. Stable expression of the receptors in mammalian cells (e.g., CHO, HEK 293) is achieved after integration of the transfected cDNA into the chromosomes of the host cells. These stable cell lines constituently express the cloned receptors and can be propagated infinitely. Stable cell lines expressing the receptor cDNAs individually can be used in the binding assay to measure the affinity and selectivity of the receptors for serotonin agonists, antagonists and enhancers. These cells can also be used in functional assay to determine the agonist activity of any ligand.

Membranes prepared from transfected (HEK 293e) cells were utilized in a binding assay to measure the affinity of the receptors for radiolabeled agonists, e.g. [3H]5HT or [3H] mesulergine. The binding assay was performed by incubating membranes with increasing concentrations of radiolabeled agonists. Bound ligand was separated from free ligand by filtration. Bound radioactivity was measured by scintillation counting. Substances which bind to or enhance binding to expressed receptors in cells can be identified in competition binding assays with radiolabeled agonists. For the competition binding assay, membranes were incubated with a fixed concentration of radioligand and various concentrations of unlabeled agonists or antagonists.

Functional assay was performed by loading the receptor-expressing with [3H]inositol, incubating the cells with a ligand and measuring the accumulation of [3H]inositol trisphsophate inside the cells.

A transient expression system can be established by microinjection of in vitro transcribed mRNA from the cloned receptor cDNAs into Xenopus oocytes. The expression system allows measurement of the biological effects upon activation of the expressed receptors with ligand binding.

In the procedure for generating the isoforms of the present invention, transcripts encoding the mouse serotonin 5-HT2c receptor subtype undergo RNA editing events in which genomically encoded adenosine residues are converted to inosines by the action of double-stranded RNA adenosine deaminases (see Burns et al., Nature vol. 387 Ma. 15, 1997 pp. 303–308, which describes rat 5-HT2c receptor isoforms resulting from RNA editing events involving transcripts encodong the serotonin receptor). Sequence analysis of complementary DNA isolates from dissected mouse brain regions have indicated the tissue-specific expression of new receptor isoforms encoded by distinct RNA species. Editing of 5-HT2c receptor messenger RNAs alters the amino acid coding potential of the predicted second intracellular loop of the receptor and can lead to altered efficacy of the interaction between receptors and their G proteins. As shown in Table 3, the 5HT $EC_{50}$ value is dependent on the amino acid sequence at position 157/159/161.

The table below compares a partial amino acid sequence of the published mouse serotonin 5-HT2c receptor (SEQ. ID No. 1) and the corresponding partial nucleotide sequence of the published mouse serotonin 5-HT2c receptor RNA, with amino acid sequences and nucleotide sequences corresponding to new isoforms of the mouse serotonin 5-HT2c receptor in the location of sequence variation. The isoforms have amino acid sequences identical to the published mouse serotonin 5-HT2c receptor polypeptide sequence except for specified amino acid replacements at one or more positions of the published mouse serotonin 5-HT2c receptor polypeptide sequence, specifically at one or more of positions 157, 159 and 161:

TABLE 1

| | Amino acid position | | | | |
| --- | --- | --- | --- | --- | --- |
| SEQ. ID No. | 157 | 158 | 159 | 160 | 161 |
| 1 (protein) | Val | Arg | Ser | Pro | Val |
| 2 (RNA) | GTG | CGT | AGT | CCT | GTT |
| 3 (protein) | Val | Arg | Asn | Pro | Val |
| 4 (RNA) | GTA/G | CGT | AAT | CCT | GTT |
| 5 (protein) | Val | Arg | Asp | Pro | Val |
| 6 (RNA) | GTA/G | CGT | GAT | CCT | GTT |
| 7 (protein) | Val | Arg | Ser | Pro | Ile |
| 8 (RNA) | GTA/G | CGT | AGT | CCT | ATT |
| 9 (protein) | Met | Arg | Asn | Pro | Ile |
| 10 (RNA) | ATG | CGT | AAT | CCT | ATT |
| 11 (protein) | Ile | Arg | Asn | Pro | Val |
| 12 (RNA) | ATA | CGT | AAT | CCT | GTT |

Alternative isoforms within the scope of the invention, otherwise identical to the natural mouse serotonin 5-HT2c receptor, have the following amino acid sequence and nucleotide sequence variations at positions 157, 159 and 161:

TABLE 2

| | Amino acid position | | | | |
| --- | --- | --- | --- | --- | --- |
| SEQ. ID No. | 157 | 158 | 159 | 160 | 161 |
| 13 (protein) | Met | Arg | Asp | Pro | Val |
| 14 (RNA) | ATG | CGT | GAT | CCT | GTT |
| 15 (protein) | Met | Arg | Asp | Pro | Ile |
| 16 (RNA) | ATG | CGT | GAT | CCT | ATT |
| 17 (protein) | Met | Arg | Gly | Pro | Val |
| 18 (RNA) | ATG | CGT | GGT | CCT | GTT |
| 19 (protein) | Met | Arg | Gly | Pro | Ile |
| 20 (RNA) | ATG | CGT | GGT | CCT | ATT |
| 21 (protein) | Met | Arg | Asn | Pro | Val |
| 22 (RNA) | ATG | CGT | AAT | CCT | GTT |
| 23 (protein) | Ile | Arg | Asp | Pro | Val |
| 24 (RNA) | ATA | CGT | GAT | CCT | GTT |

TABLE 2-continued

| | Amino acid position | | | | |
|---|---|---|---|---|---|
| SEQ. ID No. | 157 | 158 | 159 | 160 | 161 |
| 25 (protein) | Ile | Arg | Asp | Pro | Ile |
| 26 (RNA) | ATA | CGT | GAT | CCT | ATT |
| 27 (protein) | Ile | Arg | Gly | Pro | Val |
| 28 (RNA) | ATA | CGT | GGT | CCT | GTT |
| 29 (protein) | Ile | Arg | Gly | Pro | Ile |
| 30 (RNA) | ATA | CGT | GGT | CCT | ATT |
| 31 (protein) | Ile | Arg | Asn | Pro | Ile |
| 32 (RNA) | ATA | CGT | AAT | CCT | ATT |
| 33 (protein) | Val | Arg | Asp | Pro | Ile |
| 34 (RNA) | GTA/G | CGT | GAT | CCT | ATT |
| 35 (protein) | Val | Arg | Gly | Pro | Val |
| 36 (RNA) | GTA/G | CGT | GGT | CCT | GTT |
| 37 (protein) | Val | Arg | Gly | Pro | Ile |
| 38 (RNA) | GTA/G | CGT | GGT | CCT | ATT |
| 39 (protein) | Val | Arg | Asn | Pro | Ile |
| 40 (RNA) | GTA/G | CGT | AAT | CCT | ATT |
| 41 (protein) | Met | Arg | Ser | Pro | Val |
| 42 (RNA) | ATG | CGT | AGT | CCT | GTT |
| 43 (protein) | Met | Arg | Ser | Pro | Ile |
| 44 (RNA) | ATG | CGT | AGT | CCT | ATT |

TABLE 3

5HT $EC_{50}$ values (nM) for vaious isoforms of mouse 5HT2c receptor

| SEQ ID No. | Isoform | 5HT $EC_{50}$ |
|---|---|---|
| 1 | VSV | 3.5 |
| 3 | VNV | 3.1 |
| 5 | VDV | 5.9 |
| 9 | MNI | 0.9 |
| 11 | INV | 1.6 |

EXAMPLE

Mouse brain cDNA (Clonetech Catalog#7130–1) was used as a template to amplify the mouse 5HT2c receptor cDNA. The PCR oligos used in this amplification were a sense oligo 5'-CTGAAGCAATAAATGGTGGTGAACCT-GGGCACTG(SEQ. ID No. 45) which hybridizes to the start codon and several residues following the start codon and an anti-sense ologio 5'-GCCTCTAGATTTCCTGTAGGAAA-GCTGCGCTG (SEQ. ID No. 46) which hybridizes to the 3'-untranslated region following the stop codon. The PCR product thus contains a mixture of the most abundant isoforms of mouse 5HT2c receptor cDNA. To determine the sequence of mouse 5HT2c receptor cDNA, the PCR product was cut with XbaI restriction enzyme, and ligated to the vector pE3 which was treated with the restriction enzyme Stu I and XbaI.

The vector pE3 was modified from the pCEP4 vector (Cat # V044–50, Invitrogen, Carlsbad, Calif.) as described below. (1) To remove the eukaryotic expression cassette downstream of oriP segment (origin of replication from Epstein Bar virus), pCEP4 was digested with restriction enzyme Xba I and Sal I, then blunt ended with the Klenow fragment of DNA polymerase and self-ligated with T4 DNA ligase. (2) To replace the EBNA-1 (Epstein-Barr virus nuclear antigen) upstream of the oriP segment with a eukaryotic expression cassete, the resulting plasmid from step 1 was digested with restriction enzyme Xmn I and Sph I, and ligated with the XmnI-XhoI DNA fragment from pcDNA3.1 kyg(+) (Invitrogen, cat #V870-20) containing CMV (cytomegalus virus) immediate early gene enhancer-promoter region and the Xho I-BamH I fragment from pCDM8 (Invitrogen Cat #V308-20) containing the SV40 intron/poly A signal and a BamH I-Sph I linker. (3) The multiple cloning site was modified with synthetic overlapping oligos containing unique sites of Sac I, Age I, Stu I, KpnI, Xho I, Sse8387 I, Not I and Xba I. Taken together, in the final plasmid pE3, EBNA-1 is deleted, the expression cassette is moved to the upstream of oriP and transcription is in the same direction of replication.

After the mouse 5HT2c receptor PCR product has been ligated with the pE3 vector, the ligation mixture was transformed into the E. coli host DH5α. Single colonies were picked from the transformation plate, followed by plasmid DNA preparation from each clone. The sequence of the mouse 5HT2c receptor cDNA was determined by standard fluorescence-based dideoxy DNA sequencing (Perkin-Elmer, Foster City, Calif.).

The plasmid carrying mouse 5-HT2c cDNA (abbreviated as m2C-pE3) was transfected into 293-EBNA cells (Invitrogen, Cat #R620-07) by the method of lipofection. Briefly, 2 μg plasmid DNA was diluted in 400 μl Dulbecco's phophate-buffered saline and mixed with 30 μl lipofectamine reagent (GIBCO-BRL, cat #10964-913). After 20 min incubation, the mixture was diluted with 5 ml OPTI-MEM I reduced serum medium (GIBCO-BRL, cat #31985-013) and transferred to a T75 flask of 293-EBNA cells which were grown overnight. After 5–7 hr incubation at 37° C., the transfection medium was aspirated off. The cells were washed twice with growth medium and cultured for 48 hr in $CO_2$ incubator. The cells were then split and cultured in the medium containing 250 μg/ml hygromycin. The untransfected cells were killed, and the surviving cells collected for continuing culture or assaying.

A number of other cell lines are suitable for expressing mouse 5-HT2c receptors, such as CHO, HEK293, COS, or Hela cells. Transfection can also be carried out by other methods, e.g. electroporation, calcium phosphate precipitation, or DEAE-Dextran.

The recombinant 293-EBNA cells expressing mouse 5-HT2c receptors were used in receptor binding and functional assays. To prepare membranes for binding assays, the cells were homogenized in hypotonic buffer (50 mM Tris-HCl, pH7.4, 5 mM $MgCl_2$). After removal of nuclei by low speed centrifugation at 1000 g, the membranes were pelleted by centrifugation at 45,000 g for 30 min.

Ligand Binding Assays

Ligand binding assays are commonly used to determine how well a compound binds to a receptor. [3H]mesulergine or [3H] 5-HT binding assays were carried out with the mouse 5HT2c membrane preparations. Radioligand was incubated with the membranes in binding buffer (50 mM Tris-HCl, pH7.4, 5 mM MgCl, 0.1% ascorbic acid and 10 uM pargylin) in the presense or absense of unlabeled compounds. After 30 min incubation at room temperature, the binding reaction was terminated by filtering the mixture through GF/C filters. After washing off the unbound ligand, the amount of radioligand-receptor complex trapped on the filter was measured by scintilation counting. The binding affinities (Kd, $IC_{50}$ or Ki) of the compounds for mouse 5-HT2c receptor could be calculated from the binding assays.

Functional Activity Assays

Second messenger assays are used to determine the functional activity of a compound upon binding to a receptor. It is well established that 5-HT2c receptor is coupled via G-protein of Gq/11 class to phosphatidyl-inositol (PI) hydrolysis resulting in the production of two second messengers, inositol trisphosphate (IP3) and diacylglycerol (DAG). The functional activity of mouse 5-HT2c receptor was determined by measurement of the increases in the intracellular inositol phosphate level following agonist stimulation (PI assay). Transfected 293EBNA cells were seeded into multiwell plates and cultured in medium containing [3H]-myo-inositol (2 uCi/ml) for 24–72 hr. After labelling period, cells were washed, and preincubated for 30 min in balanced salt buffer containing 10 mM LiCl. Cells were then stimulated in the same buffer with agonist 5-HIT or test compounds for 45 min at 37° C. After removal of the medium, the reaction was stoped by addition of 10 mM formic acid. Cell extracts were collected after 30 min incubation at 4° C., the inositol phosphate fraction was then isolated by anion exchange chromatography and quantitated by scintillation counting. The potency (EC50) and efficacy (% maximal response) of a compound activating mouse 5-HT2c can be determined.

What is claimed is:

1. A mammalian cell membrane prepared from a mammalian cell containing a cDNA encoding a polypeptide, said polypeptide having an amino acid sequence selected from the group consisting of SEQ ID Nos. 3, 5, 7, 9, and 11, wherein said membrane comprises said polypeptide.

2. A mammalian cell membrane prepared from a mammalian cell transfected with a recombinant DNA, said recombinant DNA comprising vector DNA and a cDNA encoding a polypeptide, said polypeptide having an amino acid sequence selected from the group consisting of SEQ. ID Nos. 3, 5, 7, 9, and 11, wherein said membrane comprises said polypeptide.

* * * * *

UNITED STATES PATENT AND TRADEMARK OFFICE
CERTIFICATE OF CORRECTION

PATENT NO.   : 6,495,665 B1
DATED        : December 17, 2002
INVENTOR(S)  : Tung M. Fong, Jie Liu and Leonardus H. T. Van Der Ploeg It is certified that error appears in the above-identified patent and that said Letters Patent is hereby corrected as shown below:

<u>Title page,</u>
Item [75], delete "Tong M. Fong" and insert thereof -- Tung M. Fong --.

Signed and Sealed this

Nineteenth Day of August, 2003

JAMES E. ROGAN
*Director of the United States Patent and Trademark Office*